United States Patent
Goodwin, Jr.

(10) Patent No.: US 6,767,401 B2
(45) Date of Patent: Jul. 27, 2004

(54) CRYSTAL FORMING APPARATUS AND METHOD FOR USING SAME

(75) Inventor: Richard H. Goodwin, Jr., Bethesda, MD (US)

(73) Assignee: Neuro Probe Incorporated, Gaithersburg, MD (US)

(*) Notice: Subject to any disclaimer, the term of this patent is extended or adjusted under 35 U.S.C. 154(b) by 0 days.

(21) Appl. No.: 10/345,217

(22) Filed: Jan. 16, 2003

(65) Prior Publication Data

US 2003/0150379 A1 Aug. 14, 2003

Related U.S. Application Data

(60) Provisional application No. 60/349,252, filed on Jan. 18, 2002.

(51) Int. Cl.[7] .............................................. C30B 25/00
(52) U.S. Cl. ..................... 117/80; 422/109; 422/245.1; 425/30
(58) Field of Search ........................... 117/80; 422/109, 422/245.1, 30; 425/30

(56) References Cited

U.S. PATENT DOCUMENTS

| | | |
|---|---|---|
| 2,561,339 A | 7/1951 | Chediak |
| 3,055,808 A | 9/1962 | Henderson |
| 3,107,204 A | 10/1963 | Brown et al. |
| 3,165,450 A | 1/1965 | Scheidt |
| 4,012,288 A | 3/1977 | Lyman et al. |
| 4,299,921 A | 11/1981 | Youssef |
| 4,599,315 A | 7/1986 | Terasaki et al. |
| 4,682,891 A | 7/1987 | de Macario et al. |
| 4,770,856 A | 9/1988 | Uthemann et al. |
| 4,822,741 A | 4/1989 | Banes |
| 4,886,646 A | 12/1989 | Carter et al. |
| 5,096,676 A | 3/1992 | McPherson et al. |
| 5,221,410 A | 6/1993 | Kushner et al. |
| 5,284,753 A | 2/1994 | Goodwin, Jr. |

Primary Examiner—Felisa Hiteshew
(74) Attorney, Agent, or Firm—Shaw Pittman LLP

(57) ABSTRACT

A crystal forming apparatus and method for using the apparatus, the apparatus including a plate and a film. The plate has a site adapted to hold a screening solution. The film is adjacent to the plate. The film seals the site and is adapted to contain a precipitant solution inside the site with an air gap between the screening solution and the precipitant solution. In a preferred embodiment, the film is transparent. In another preferred embodiment, the plate comprises a second transparent film supported by a lattice structure and the precipitant solution is sandwiched between the two films.

22 Claims, 11 Drawing Sheets

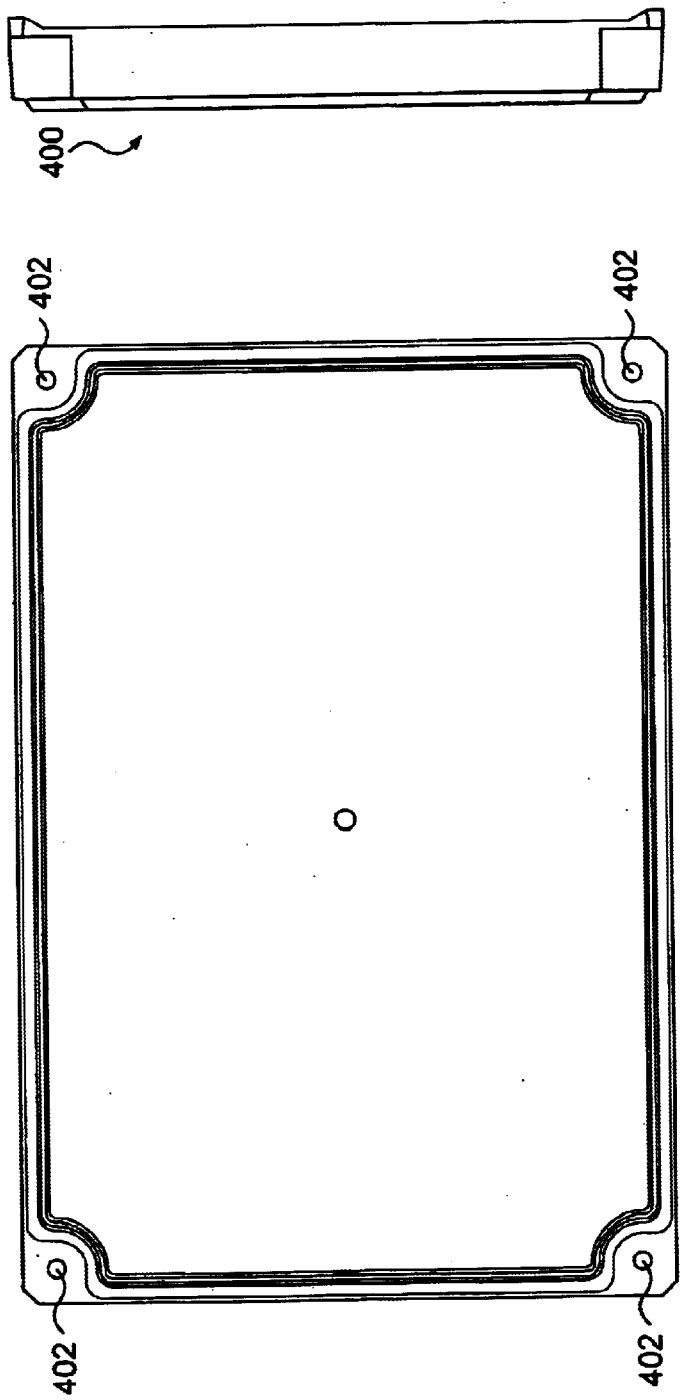
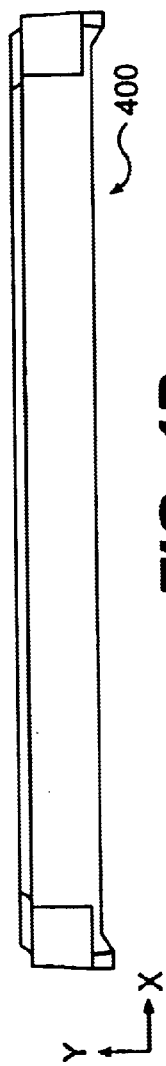
FIG. 4C
FIG. 4A
FIG. 4B

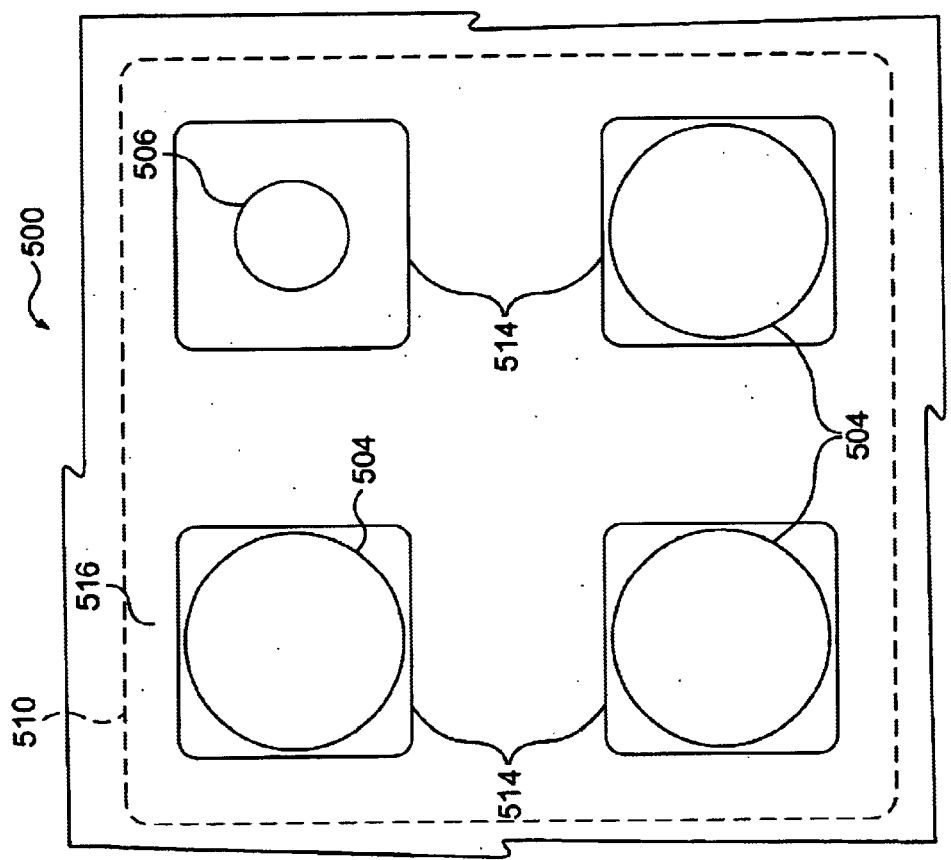

SECTION 5C-5C

SECTION 5D-5D

CRYSTAL FORMING APPARATUS AND METHOD FOR USING SAME

This application claims the benefit of U.S. Provisional Application No. 60/349,252, filed Jan. 18, 2002, which is herein incorporated by reference in its entirety.

BACKGROUND

1. Field of the Invention

The present invention relates generally to crystallization chambers and to apparatus and methods for conducting multiple crystal forming experiments.

2. Background of the Invention

There remains a need in the prior art for a fast, reliable, and cost-effective crystallization apparatus that enables a researcher to conduct multiple crystal forming experiments, with minimal set-up effort and small amounts of sample solutions. Small sample size is particularly important in protein crystallization, where the protein is scarce and very expensive, and one kind of protein is used with, for example, two thousand different crystal growing solutions to ascertain which ones promote crystal growth. In the specific context of crystallization apparatus that use multiple-well microplates (see, for example, U.S. Pat. No. 5,221,410 to Kushner et al., which is incorporated by reference herein), there remains a need for a crystallization apparatus that is fast, reliable, and easily automated, yet can also be used with manual methods. Specifically, there is a need for an apparatus that is compatible with robotic systems that dispense small volumes of sample solutions and detect the presence of very small crystals.

SUMMARY OF THE INVENTION

According to a representative embodiment, the present invention is a crystallization apparatus, as well as a method for using the apparatus, that provides a film on which to place sample solutions. In addition to the film, the apparatus can include other components on which complementary solutions can be placed, and which, together with the film, form a plurality of independent crystallization environments or sites. The apparatus and method can be adapted to perform, for example, hanging drop, sitting drop, or sandwich drop vapor diffusion crystallization. As used herein, sandwich drop refers to a drop that contacts an upper and lower surface.

An embodiment of the present invention provides a crystal forming apparatus that includes a plate and a film. The plate has a site adapted to hold a screening solution. The film is adjacent to the plate. The film seals the site and is adapted to contain a precipitant solution inside the site with an air gap between the screening solution and the precipitant solution.

In an aspect of this embodiment, the plate is a microplate and the site is a well of the microplate. A sample of screening solution can be disposed in the well and a sample of precipitant solution can be held by the film and suspended over the sample of screening solution.

In another aspect of this embodiment, the plate is a second film supported by a first support structure. The first film is supported by a second support structure. The second support structure is disposed on top of the second film. The first film is disposed on a side of the second support structure opposite the second film. The second support structure and the first film are adapted to seal the site. The second support structure is, for example, a lattice having a first through-hole, a second through-hole, and a passageway connecting the first through-hole to the second through-hole.

Another embodiment of the present invention provides a method for forming crystals that includes depositing a screening solution into a well of a microplate, depositing a precipitant solution onto a film, and placing the film over the well such that the precipitant solution is suspended over the screening solution.

Another embodiment of the present invention provides a method for forming crystals that includes depositing a screening solution onto a first film, depositing a precipitant solution onto the first film proximate to the screening solution, sealing the screening solution and the precipitant solution within a site between the first film and a second film, and providing, within the site, an air gap between the screening solution and the precipitant solution.

BRIEF DESCRIPTION OF THE DRAWINGS

FIG. 4A is a schematic diagram of an exemplary lid for a crystallization apparatus, according to an embodiment of the present invention.

FIGS. 4B and 4C are schematic diagrams of side views of the exemplary lid shown in FIG. 4A.

FIG. 5B is a schematic diagram of the crystallization apparatus of FIG. 5A, with the top plate and top film removed.

DETAILED DESCRIPTION OF THE INVENTION

An embodiment of the crystallization apparatus of the present invention includes a microplate with greased rims and a film bonded to a frame. The frame is mounted on top of the microplate, such that the film contacts the greased rims of the microplate to create individual, independent environments in which crystals may form. In a further embodiment, the apparatus includes a lid placed over the frame to protect the frame, film, and microplate, and to allow one apparatus to be stacked on top of another.

Figure 1A:
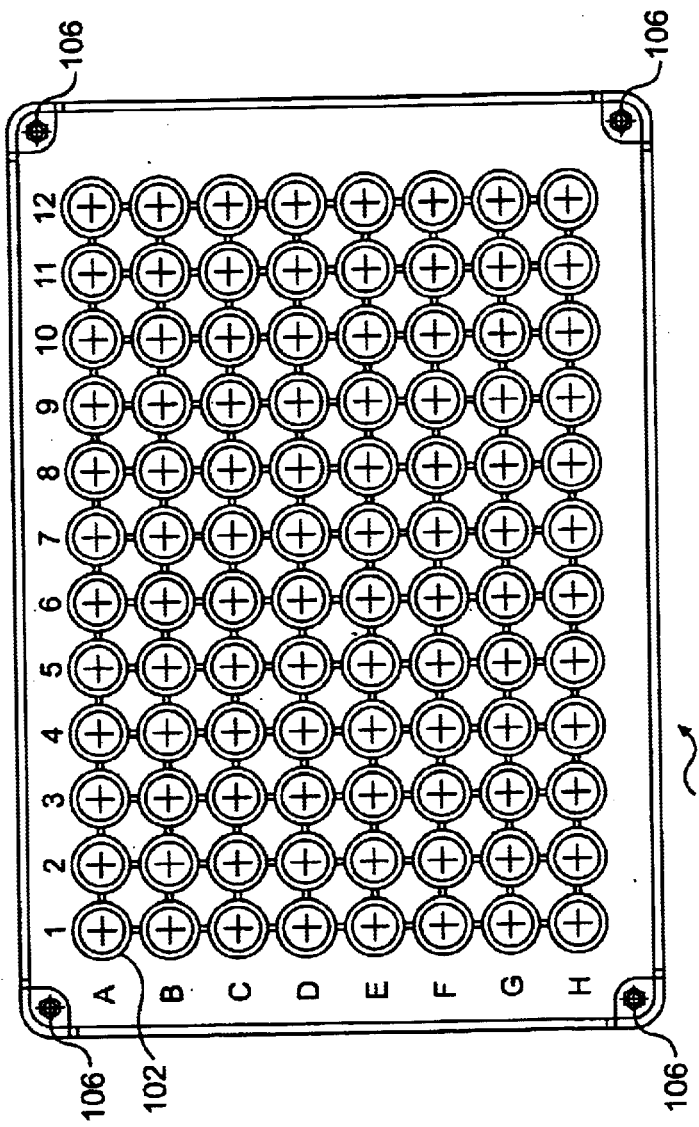
FIG. 1A is a schematic diagram of a top view of an exemplary microplate of a crystallization apparatus, according to an embodiment of the present invention.
Figure 1B:
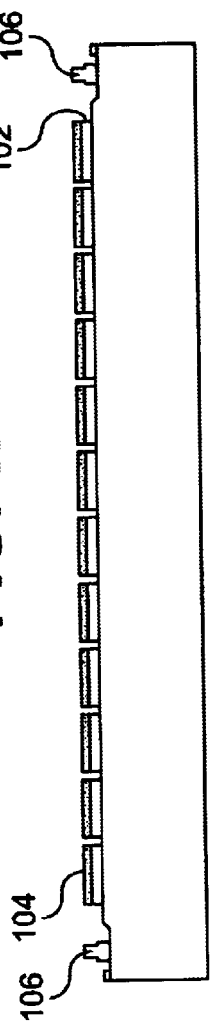
FIGS. 1B and 1C are schematic diagrams of side views of the exemplary microplate shown in FIG. 1A.
Figure 1C:
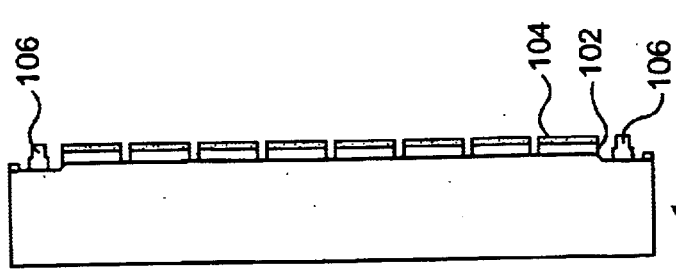

FIGS. 1A, 1B, and 1C illustrate a microplate 100, according to an embodiment of the present invention. As shown, microplate 100 has rims 102, each of which is covered with a layer of grease 104. In a specific embodiment, the microplate 100 is a polystyrene 96-well microplate with greased rims. Grease 104 is any material suitable for sealing a gap between a film and rims 102. Grease 104 could be, for example, a malleable sealant with adhesive properties. Grease 104 could also be a gasket with adhesive properties. In an alternative embodiment, if the materials of a film and the rims 102 can contact each other and provide an adequate seal, then grease 104 is not needed.

Microplate 100 also has reference pins 106 for aligning and retaining a frame. Although, in this example, microplate 100 has four pins 106, microplate 100 could, of course, have as many pins (at least two, but could also be three, four, or more) as needed to properly align and retain a frame. In addition, microplate 100 could use other alignment/retention means, such as adhesives, interference fits, or interlocking or inter-locating components or features.

Figure 2:
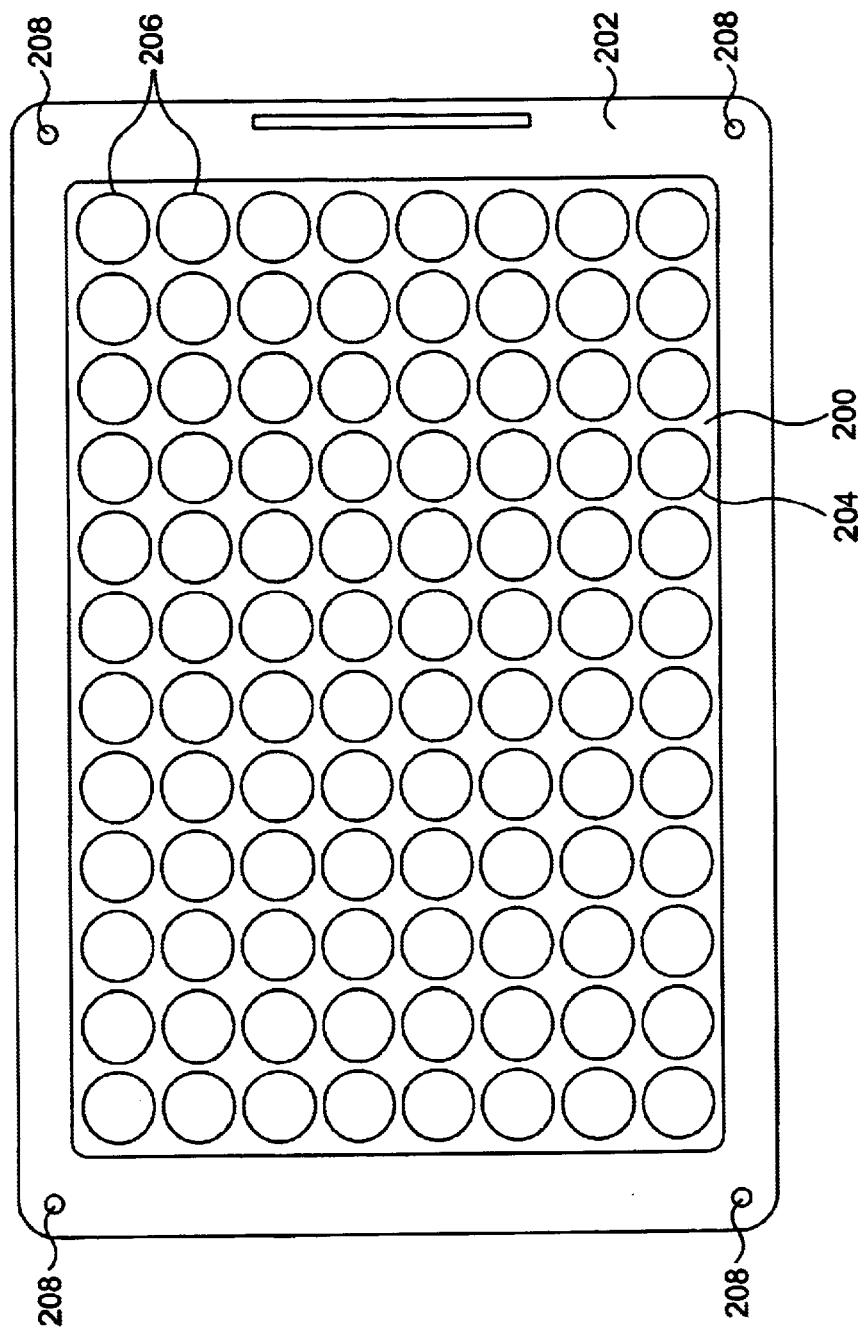
FIG. 2 is a schematic diagram of an exemplary film and frame of a crystallization apparatus, according to an embodiment of the present invention.

FIG. 2 illustrates a film 200 bonded to a frame 202, according to an embodiment of the present invention. In a specific embodiment, film 200 is Teflon™, e.g., 0.001" Teflon™. As shown in FIG. 2, film 200 preferably has marked positioning rings 204, which are, for example, silk-screened in ink on top of film 200. These positioning rings 204 correspond to the well configuration of the microplate on which film 200 and frame 202 are to be mounted, and help guide placement of precipitant solutions onto film 200. Markings (e.g., in the example shown in FIG. 2, numbers and letters) assist in monitoring the particularities of each site.

As used herein, a precipitant solution refers to a solution of a compound that is to be crystallized, and a screening solution refers to a solution that may or may not solubilize the compound to promote crystallization. For example, in the context of protein crystallization screening, in which a goal is to identify solutions (from among many possible screening solutions) that solubilize a protein, a protein solution, which is relatively concentrated, is typically mixed 50:50 with each of the possible screening solutions. This 50:50 solution is the precipitant solution and is placed in a site along with its corresponding 100% screening solution, where vapor diffusion then begins.

Positioning rings 204 provide multiple crystallization sites. The terms "test site" or "site" are used herein to refer to a delineated spot on a film where a precipitant solution is positioned. The position of the sites is defined by, for example, a pattern 206 on film 200. The pattern 206, which identifies the locations of the sites, may be formed by ink imprinted on the film, may be a patterned film of plastic or silicone, or may be defined by a patterned hydrophobic coating silk-screened or otherwise applied to the film. The coating may simply define the locations of the test sites, or it may also function as a hydrophobic barrier, spatially restricting a precipitant fluid.

Frame 202 is rigid enough to keep film 200 flat, to ensure that film 200 adequately covers each well of microplate 100 when the components are assembled (described in more detail below). While keeping film 200 flat, at the same time, frame 202 can allow film 200 some degree of movement (e.g., by having slack, flexibility, or elasticity) in a direction generally perpendicular (normal) or at an angle to the face of film 200. Frame 202 includes reference holes 208, which engage reference pins 106 of microplate 100 to align the components during assembly. Frame 202 can be any formable material, such as plastic, stainless steel, or aluminum. In a specific embodiment, frame 202 is an anodized aluminum frame. Film 200 can be attached to frame 202 by any suitable fastening means, including glue, adhesives, heat seals, ultrasonic seals, or mechanical means.

Figure 3A:
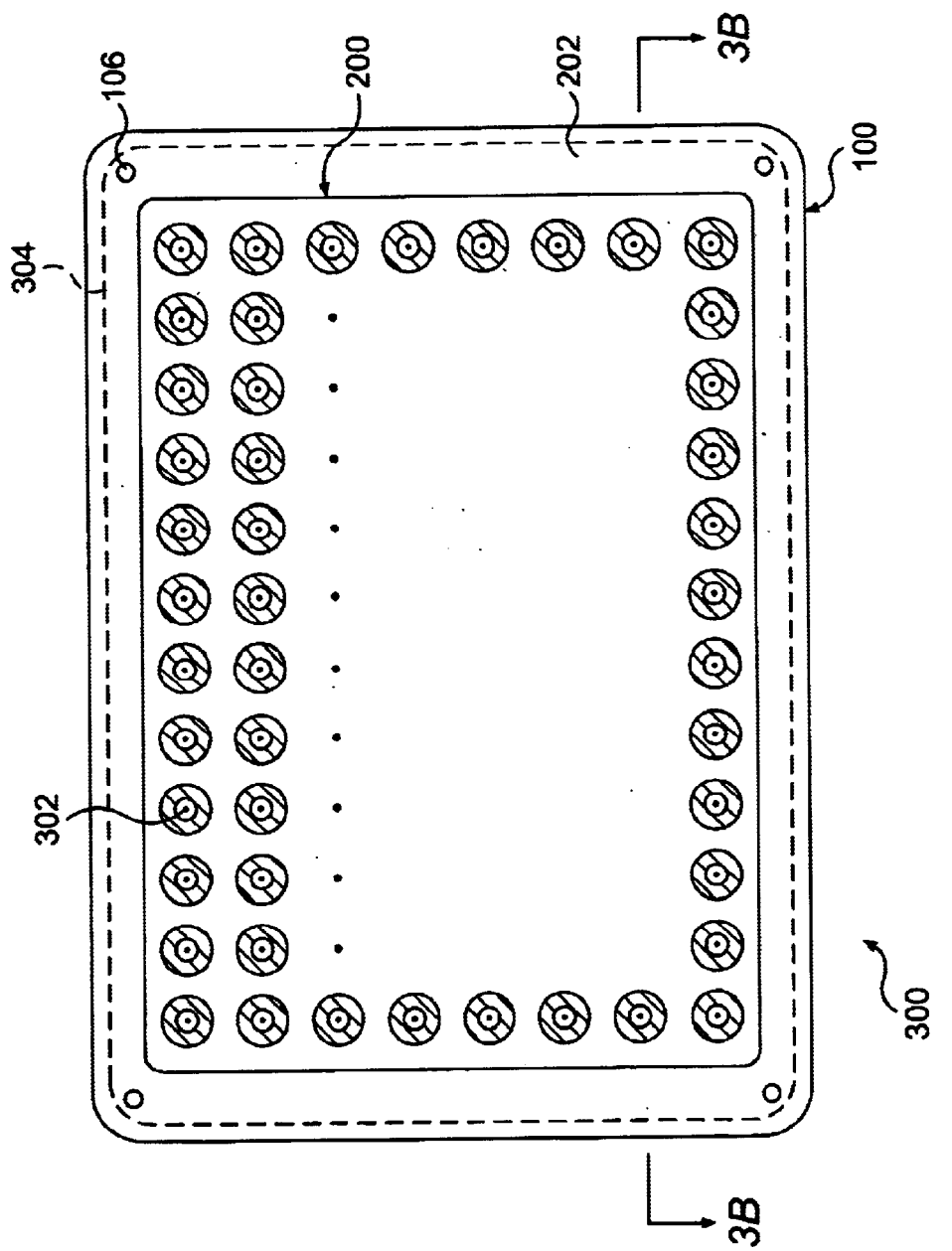
FIG. 3A is a schematic diagram of an exemplary crystallization apparatus, according to an embodiment of the present invention.

FIG. 3A illustrates an assembled multiple-site crystallization apparatus 300, according to an embodiment of the present invention. As shown, frame 202 of FIG. 2 is mounted on top of microplate 100 of FIG. 1A to provide multiple-site crystallization apparatus 300.

In this embodiment, apparatus 300 includes microplate 100 having ninety-six wells 302, a rim 304 around microplate 100, four reference pins 106, and an overlaying film 200 surrounded by a frame 202. Although not shown in FIG. 3A, apparatus 300 could also include a lid over frame 202, to protect the test sites and provide a surface on which to stack another microplate.

Figure 3B:
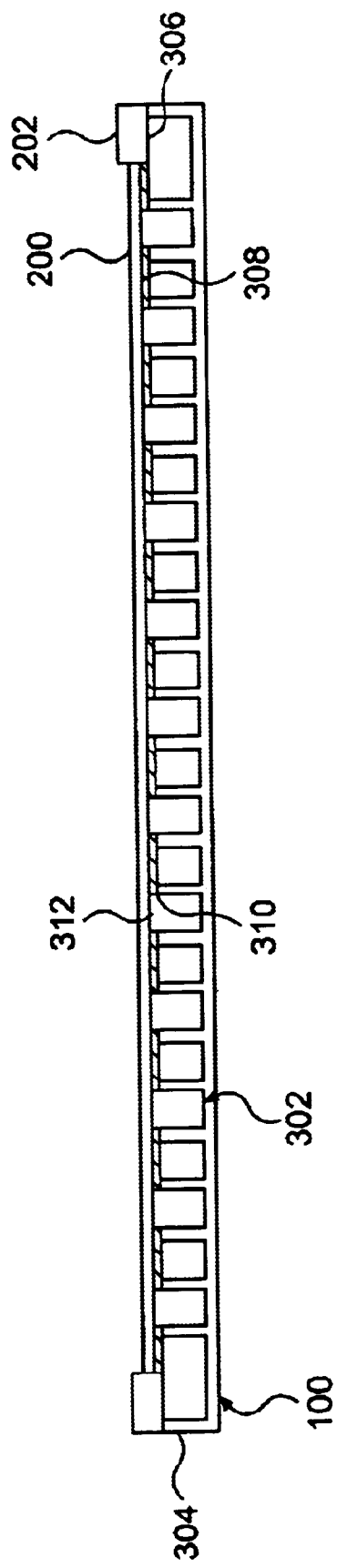
FIG. 3B is a schematic diagram showing a cross-sectional view of the crystallization apparatus shown in FIG. 3A along line 3B—3B.

FIG. 3B is a cross-sectional view of the embodiment of FIG. 3A taken along line 3B—3B, with frame 202 and film 200 on top of microplate 100. Optionally, frame 202 is secured to microplate 100 with a layer of pressure-sensitive adhesive 306. FIG. 3A shows how reference pins 106 align microplate 100 and framed film 200. Although FIGS. 3A and 3B show microplate 100 as having cylindrical wells, as one of ordinary skill in the art would appreciate, the wells could be any number of shapes, e.g., the wells could be oval or cubical with radiused corners.

In FIG. 3A, frame 202 with the attached film 200 is positioned over microplate 100 so that rim 304 of microplate 100 is under frame 202. Microplate 100 may be manufactured from any rigid material that is not biologically or chemically active with the screening solutions and is not water-soluble, e.g., glass, sapphire, acrylic, polystyrene, or polycarbonate. Microplate 100 has a plurality of wells 302 (in this example, ninety-six). The position and spacing of the wells is preferably a standard spacing, e.g., the standard spacing for 96-well microplates (e.g., 9 mm center to center), and the outside dimensions of frame 202 are preferably (although not necessarily) identical to the dimensions of standard microplates, so that automatic equipment can be used to handle frame 202 and microplate 100.

According to an embodiment of the method of the present invention, the exemplary crystallization apparatus shown in FIGS. 1A–3B is used as follows. First, the wells of microplate 100 are filled with an appropriate volume of crystal growing (screening) solution. Preferably, each well of microplate 100 is filled with a different crystal growing (screening) solution, to test the efficacies of the different crystal growing solutions with respect to a particular compound (e.g., a particular protein).

Film 200 is then placed upside down and precipitant solutions are pipetted onto the centers of positioning rings 204. Proper placement of the drops on film 200 can be accomplished with a hand-held pipette, an automatic variable-volume pipette, or an automatic pipetting machine. The Kushner patent, incorporated by reference above, contains several examples of crystal growth procedures.

Next, frame 202, with the attached film 200, is inverted and pressed onto the four corner reference pins 106 of microplate 100. With frame 202 pressed onto microplate 100, the ring 102 at each site preferably makes full contact with film 200. If, for some reason, a ring 102 does not fully contact film 200, then film 200 is gently pressed until the ring 102 makes complete contact. Although frame 202 keeps film 200 relatively flat, film 200 still possesses some "give" (e.g., some amount of elasticity, flexibility, or slack) that enables film 200 to move and better contact ring 102, to provide a good seal. If necessary for this seal, as described above, grease 104 can be disposed between film 200 and rings 202.

With frame 202 inverted and mounted on microplate 100, and with film 200 sealing the wells of microplate 100, the vapor diffusion process can begin. In this configuration, at each site, the precipitant solution (e.g., 50% protein solution and 50% screening solution of the associated site) is suspended from film 200 over the crystal growing solution (e.g., 100% screening solution) in the bottom of the wells of microplate 100. An air gap separates the two solutions. During vapor diffusion, vapor travels from the precipitant solution through the air gap to the crystal growing (screening) solution. This process of vapor diffusion concentrates the compound in the precipitant solution. In efficacious crystal growing solutions, the crystallization point is reached, and crystals begin to form.

A further embodiment of the present invention includes a lid that covers the microplate to protect grease from being rubbed off the rims before the frame is mounted on the microplate. FIGS. 4A, 4B, and 4C illustrate an exemplary lid 400, which covers the microplate 100 shown in FIGS. 1A–1C. Lid 400 has four reference openings 402 at its corners, which fit over the four corner reference pins 106 of microplate 100. Thus, a user can keep lid 400 over microplate 100 before using microplate 100, thereby protecting the test sites, the rings 102, the layer of grease 104, and any solution in the sites (see FIGS. 1B and 1C). Lid 400 also protects the test sites after solutions have been added and after frame 202 has been placed on microplate 100. Lid 400 can also provide a platform on which additional apparatus can be stacked, one on top of another, which is especially useful for automated robotic applications.

In a further embodiment of the present invention, film 200 is coated with a semi-hydrophobic material such that when a drop of precipitant solution is placed on film 200, the drop maintains its round shape, instead of leveling out and forming an elongated shape. The semi-hydrophobic material is not so hydrophobic that the drop would fall off if film 200 is inverted. Rather, the semi-hydrophobic material enables the drop to remain attached to film 200 when film 200 is inverted, and helps to keep the round shape of the drop. An example of a semi-hydrophobic material suitable for this purpose is a transparent polymer material, such as Rain-X™ Original Glass Treatment produced by Blue Coral-Slick 50, Ltd. of Cleveland, Ohio.

In a further embodiment of the present invention, a portion of film 200 is covered or partially covered (e.g., in a pattern such as a ring pattern) with a hydrophobic material to delimit areas in which to place and hold the precipitant solution. For example, referring to FIG. 2, the areas inside positioning rings 204 are partially covered with a hydrophobic material, leaving round spots in the center uncovered. The spots in the center are naturally hydrophilic, or are rendered so by coating them with a hydrophilic material. The diameter of the hydrophilic area is varied to produce ideal drop configuration for a given volume of precipitant solution. For example, a 1 mm spot holds a drop of between 0.5 and 1.0 microliters, while a 2 mm diameter spot holds a drop of between 4 and 6 microliters. This hydrophobic/hydrophilic configuration causes drops of precipitant solution to self-center and assume an ideal shape when placed on film 200, within positioning rings 204. Positioning rings 204 act as guides in placing drops at the individual sites, with the smaller hydrophilic areas within the rings precisely positioning the drops.

FIG. 3B illustrates an example of this embodiment. As shown, the bottom surface 308 of the film 200 is partially covered with a patterned hydrophobic coating 310. Hydrophobic coating 310 is patterned to create a number of uncoated test sites 312 corresponding to the location of wells 302 in microplate 100. When drops of precipitant solution are pipetted onto surface 308 (when film 200 is inverted) at the uncoated sites 312, the drops are prevented from moving outside the perimeter of the test sites and contacting each other, and are forced into an optimal shape.

In a further embodiment of the present invention, a portion of film 200 is covered or partially covered (e.g., patterned) with a layer of material that delimits areas in which to place and hold the precipitant solution. Furthermore, the layer of material acts as a physical barrier that contains the precipitant solution. For example, referring to FIG. 2, the area outside of positioning rings 204, or any desirable area, could be covered with a film or coating of measurable thickness. The area inside the positioning rings 204 could be hydrophilic or covered or partially covered or coated with a hydrophilic material or a material with a high affinity for the precipitant solution. It would be preferable if the area inside the positioning rings were transparent or coated or covered partially or entirely with a transparent material. This hydrophobic/hydrophilic or pseudo-well/hydrophilic/high affinity configuration causes drops of precipitant solution to self-center when placed on film 200, within positioning rings 204.

In a further embodiment of the present invention, after placing screening solutions and solutions with the compound to be crystallized at each site, assembling the components, incubating and (possibly) growing crystals, film 200 can be cut away at any site location. This cut-away portion of the film, with its attached sample, can then be removed for closer examination, while leaving the remaining samples undisturbed. Furthermore, after this examination, the film and sample can be placed back onto the site from which it was removed to continue with the crystal forming process.

In a further embodiment of the present invention, lid 400 and microplate 100 are made from materials that have good-to-excellent optical qualities, e.g., polystyrene, TPX, acrylic, and other plastics, and glass, sapphire, and quartz.

In a further embodiment of the present invention, one or multiple frames can be attached to a microplate or lower plate-like component, e.g., film bonded to frames that can be oriented in either the X or Y dimension of the plate in strips, to allow for partial or staggered use of the apparatus. In this multiple frame configuration with a strip layout, the frame could be made as an injection-molded piece with formed wells, with the film bonded to the frame at the bottom of the wells. Instead of using the above-described grease, the wells could be sealed to the lower plate using o-rings or something functionally equivalent.

In a further embodiment of the present invention, microplate 100 is replaced by another frame with film bonded to it, to create a plate-like component that holds solutions in a plurality of sites. The sites can be defined by, for example, hydrophobic material, hydrophobic ink, grease rings, or other chemical or physical structures that can be applied to the film. In this case, instead of grease 104 sealing a gap between film 200 and rims 102, grease 104, or some functional equivalent, would seal the gap between the two films.

In a further embodiment of the present invention, frame 202 does not have the hollow center that is shown, for example, in FIG. 2. Instead, frame 202 has interconnecting lattices with spaces between the lattices in any numerous combinations of patterns using interconnecting segments and open spaces. The test sites fall within the spaces. FIGS. 5A–5D illustrate an example of this embodiment of the present invention, with solutions held between a first film supported by a latticed bottom plate and a second film supported by a latticed top plate.

Figure 5A:
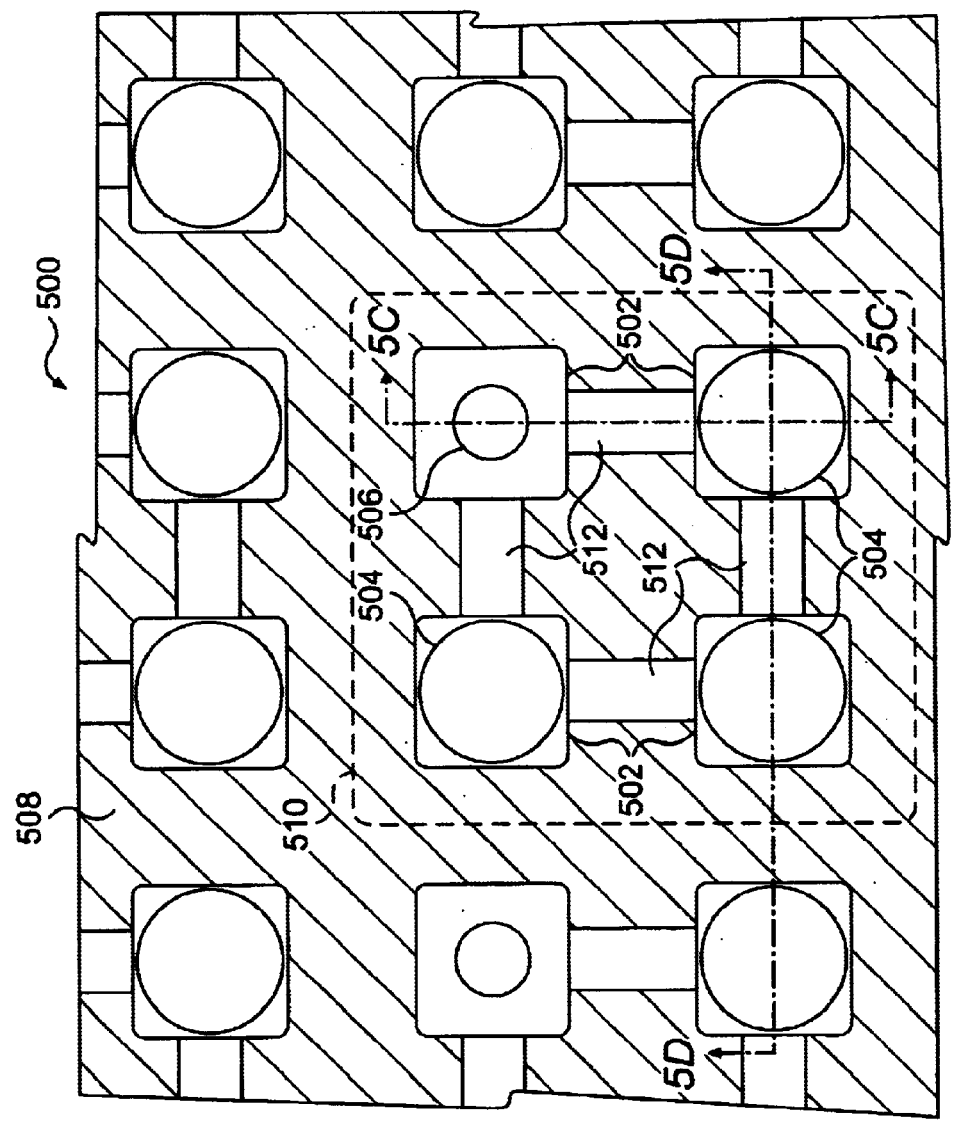
FIG. 5A is a schematic diagram of a top view of a portion of an exemplary crystallization apparatus having two films, according to an embodiment of the present invention.

FIG. 5A shows a top view of a portion of an apparatus 500 according to this embodiment of the present invention. This top view looks down through the transparent top film 528 that is supported from underneath by the top plate 526 and bonded to the top plate 526 with bonding agent 532 (see FIGS. 5C and 5D discussed below). Through-holes 502 are areas in which the bottom surface of the top film is not supported by the top plate, i.e., there is a hole in the top plate. A screening solution 504 (e.g., 100% screening solution) and a precipitant solution 506 (e.g., 50% screening solution and 50% protein solution) are disposed within through-holes 502.

In area 508, the bottom surface of the top film is supported by and bonded to the top plate. Preferably, in area 508, the bottom surface of the top film is bonded to the top plate with an adhesive.

In this example, four through-holes 502 are used for a single crystallization site, as represented by the single site 510. Within this site 510, air passages 512 (or air gaps) connect through-holes 502. Air passages 512 can be created by, for example, etching the top plate in these areas and removing half of the thickness of the plate, or by molding depressions in the top side of the lattice that forms the top plate. Preferably, an adhesive seal between the top plate and the top film provides a seal for single site 510 that isolates four through-holes 502 from the remaining sites and through-holes of apparatus 500.

FIG. 5B illustrates apparatus 500 with the top plate and film removed, showing a view of the bottom film supported by the bottom plate, with screening solution 504 and precipitant solution 506 resting on top of the bottom film. Through-holes 514 in the bottom plate substantially align with through-holes 502 of the top plate. Through-holes 514 are areas in which the bottom surface of the bottom film is not supported by the bottom plate, i.e., there is a hole in the bottom plate. At each site, screening solution 504 and precipitant solution 506 are disposed over through-holes 514, and are preferably held in place using a hydrophobic mask. In area 516, the bottom surface of the bottom film is supported by the bottom plate. Preferably, in area 516, the bottom surface of the bottom film is partially or fully bonded to the bottom plate with an adhesive.

Figure 5C:
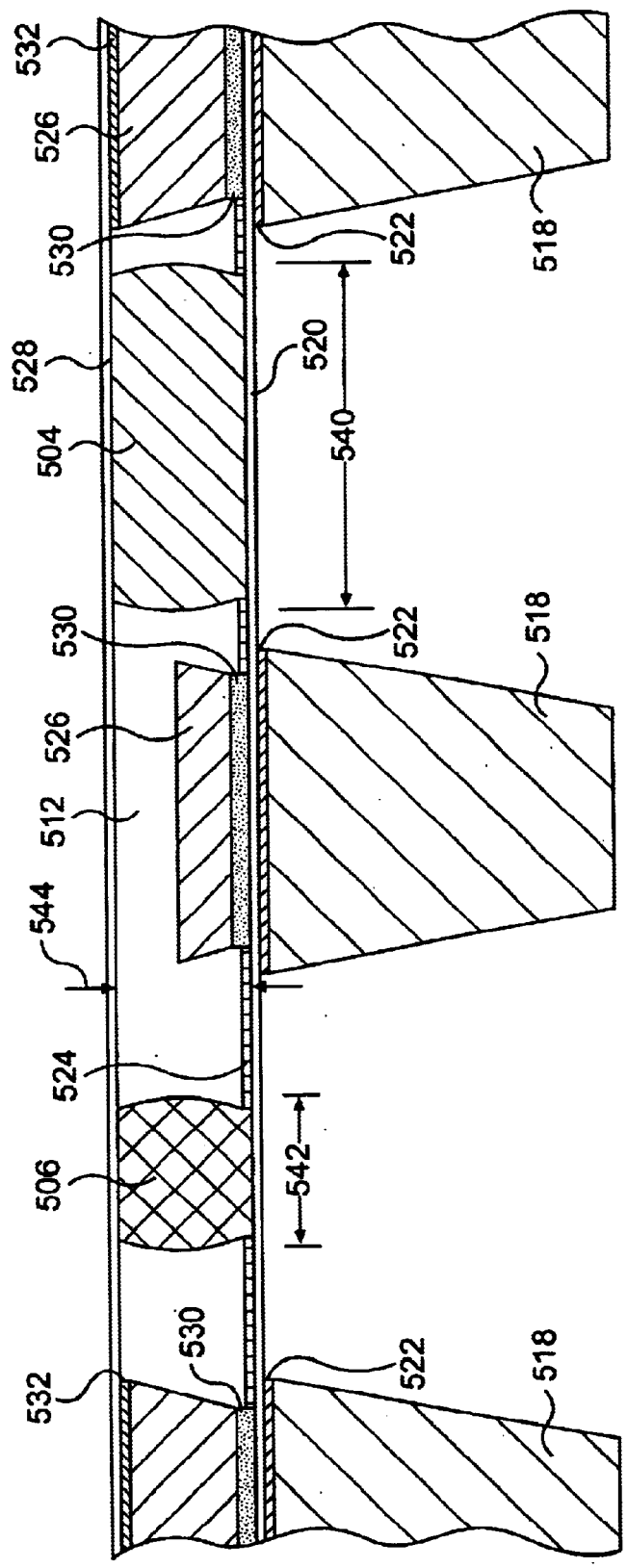
FIG. 5C is a schematic diagram of a cross-sectional view of the crystallization apparatus of FIG. 5A along line 5C—5C.
Figure 5D:
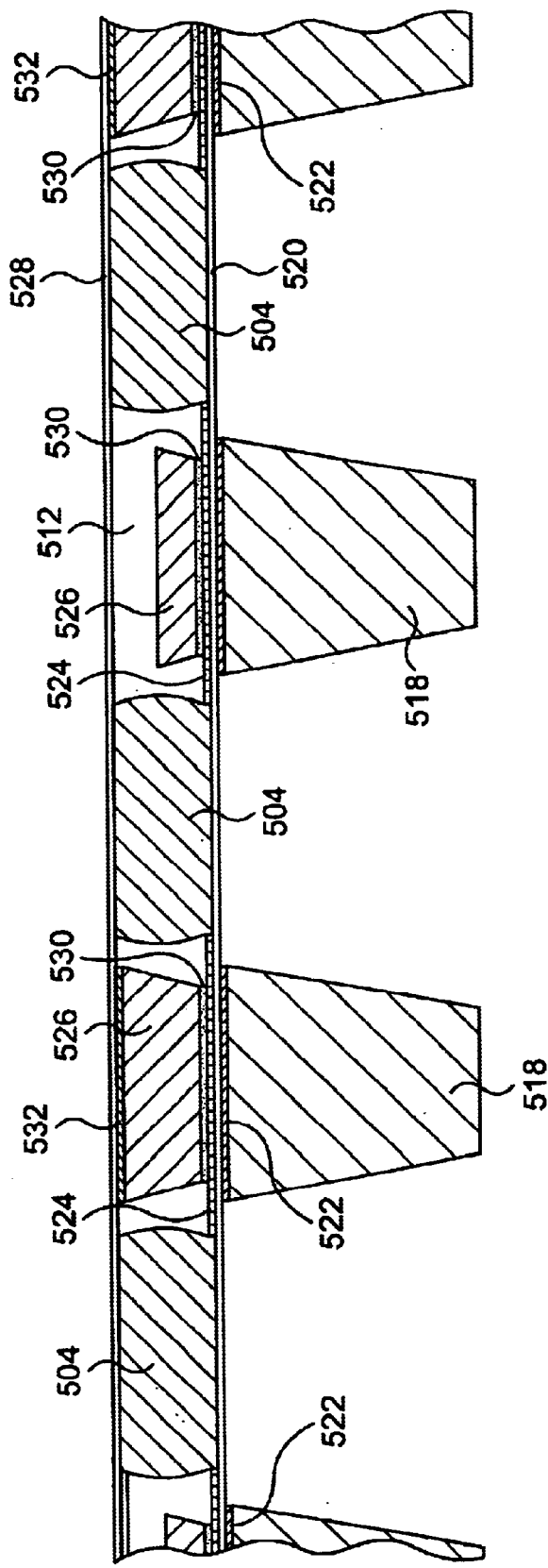
FIG. 5D is a schematic diagram of a cross-sectional view of the crystallization apparatus of FIG. 5A along line 5D—5D.

FIGS. 5C and 5D illustrate cross-sectional views of apparatus 500 along line 5C—5C and line 5D—5D (identified in FIG. 5A), respectively. As shown, bottom plate 518 is bonded to bottom film 520 with an adhesive 522. Screening solution 504 and precipitant solution 506 are disposed on bottom film 520 in the area of through-holes 502 and 514. Preferably, a hydrophobic mask 524 is applied to bottom film 520 to hold solutions 504 and 506 in place.

Top plate 526 is disposed on top of bottom film 520. In a preferred embodiment, top plate 526 is bonded to bottom film 520 with a pressure sensitive adhesive or grease 530. Top plate 526 supports top film 528, which is located on the side of top plate 526 opposite bottom film 520. Top film 528 is preferably bonded to top plate 526 with an adhesive 532.

When top plate 526 and its top film 528 are placed on top of bottom film 520, solutions 504 and 506 are disposed within through-holes 502 of top plate 526 and are sandwiched between and in contact with the bottom surface of top film 528 and the top surface of bottom film 520. As shown in FIGS. 5C and 5D, in this configuration, air passages 512 are created between adjacent through-holes 502 of site 510. Vapor diffusion through these passages 512 and around solutions 504 and 506 promotes the concentration of the target compound in solution 506 and, if successful, the crystallization of that compound.

An exemplary implementation of the embodiment of FIGS. 5A–5D uses a 384-site plate for top plate 526 and bottom plate 518. In this example, as shown in FIG. 5C, the width 540 of screening solution 504 is approximately 1.0 mm and the width 542 of precipitant solution 506 is approximately 0.500 mm. The distance 544 between the bottom top film 528 and the top of bottom film 520 is approximately 0.375 mm. As an example, this configuration creates spaces for samples of about 100 nl of precipitant solution 506 and 400 nl of screening solution 504.

Although FIGS. 5A–5D illustrate a single crystallization site having four sub-sites (i.e., through-holes in which the solutions are disposed), one of ordinary skill in the art would appreciate that a site could include two or more through-holes.

According to an embodiment of the present invention, the exemplary crystallization apparatus shown in FIGS. 5A–5D is used as follows. First, screening solution 504 is deposited on bottom film 520 within the boundaries of the hydrophobic mask 524. In this example, for site 510, three samples of the same screening solution 504 are deposited on bottom film 520 in locations corresponding to three of the four through-holes 514 of the bottom plate 518 within the single site 510. Next, the precipitant solution 506 is deposited on bottom film 520 within the boundaries of the hydrophobic mask 524. In this example, for site 510, one sample of precipitant solution 506 is deposited on bottom film 520 in a location corresponding to the fourth through-hole 514 of the bottom plate 518 within the single site 510.

With the screening and precipitant samples in place, top plate 526 and top film 528 are placed over bottom film 520 and bottom plate 518 such that through-holes 514 of bottom plate 518 and through-holes 502 of top plate 526 are aligned. Preferably, reference pins in bottom plate 518 and corresponding reference holes in top plate 526 facilitate this alignment. Alternatively, bottom plate 518 is held and positioned in a carrier plate (not shown) and top plate 526 is positioned exactly over bottom plate 518 by that carrier plate when it is placed on top of bottom film 520 and bottom plate 518. Placing top plate 526 on bottom film 520 seals site 510 within bottom film 520, top plate 526, and top film 528. In a preferred embodiment, a sealant is used between bottom film 520 and top plate 526 to help facilitate this seal. The sealant could be, for example, a pressure sensitive adhesive, a malleable sealant with adhesive properties, a gasket with adhesive properties, grease, oil, a gasket, other sealants, or combinations of such sealants.

With top plate 526 and top film placed over bottom film 520, the samples of screening solution 504 and precipitant solution 506 are sandwiched between bottom film 520 and top film 526. The vapor diffusion process then begins. In this configuration, air gaps provided by air passages 512 separate the screening solution samples from the precipitant solution samples at each site. Vapor diffusion from precipitant solution 506 to screening solutions 504 concentrates precipitant solution 506, potentially creating a crystal forming condition.

In an alternative embodiment of the method for forming crystals associated with FIGS. 5A–5D, the samples of screening solution and precipitant solution are first deposited on the bottom surface of top film 528, instead of on the top surface of bottom film 520. Top plate 526 and top film 528 would be inverted for this first step. In addition, the bottom surface of top film 528 preferably would have a hydrophobic mask to contain and position the samples. After depositing the samples on the bottom surface of top film 526, the top plate 526 and top film 528 are inverted and placed over bottom film 520. The samples are thereby sealed between bottom film 520, top plate 526, and top film 528, and the vapor diffusion process begins.

Figure 6:
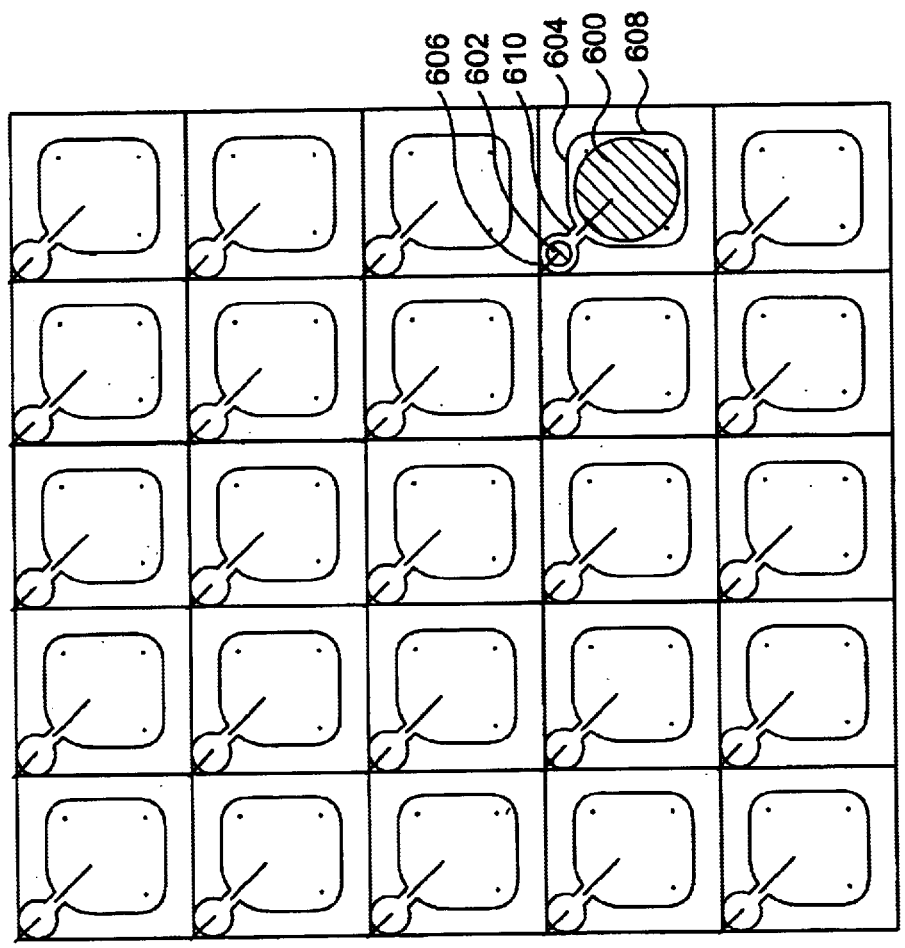
FIG. 6 is a schematic diagram of a top view of a portion of another exemplary crystallization apparatus having two films, according to an embodiment of the present invention.

FIG. 6 illustrates another embodiment of the present invention using a first film supported by a latticed bottom plate and a second film supported by a latticed top plate. As shown, this embodiment disposes a screening solution 600 and a precipitant solution 602 within a single through-hole 604 of a top plate. Preferably, a hydrophobic mask on the top surface of the bottom film holds solutions 600 and 602 in place within the through-hole 604. Through-hole 604 includes a first chamber 606 and a second chamber 608 connected by an air passage 610. In this manner, vapor solution can flow from precipitant solution 602 through air passage 610 and to screening solution 600, to promote crystal growth within the first chamber 606. Also, preferably, through-hole 604 is isolated from its surrounding through-holes by an adhesive seal around through-hole 604. The apparatus of FIG. 6 is used in a manner similar to the methods described above in reference to FIGS. 5A–5D.

Returning to FIG. 2, in another embodiment of the present invention, frame 202 has a component design that enables different films to be applied to different sites. For example, rather than being a single piece, frame 202 could include an outside frame into which one or more inner frames are inserted. The outside frame could have a portion of its opening covered with film, or could have no film at all. Each inner frame could have a different type of film, and could be interchangeably placed within the outer frame. In this manner, a researcher can use various configurations of the inner frames to cover different test sites of a single apparatus with different films.

In a further embodiment of the present invention, the components of the apparatus are configured to accommodate sitting drop and sandwich drop formats. For example, when top plate 526 of FIGS. 5A–5D is made thicker, the apparatus becomes a sitting drop configuration, or alternatively, if the sample volume of the precipitant solution 506 is reduced so that it does not contact the bottom of top film 528 of top plate 526, the apparatus provides a sitting drop configuration.

Figure 7:
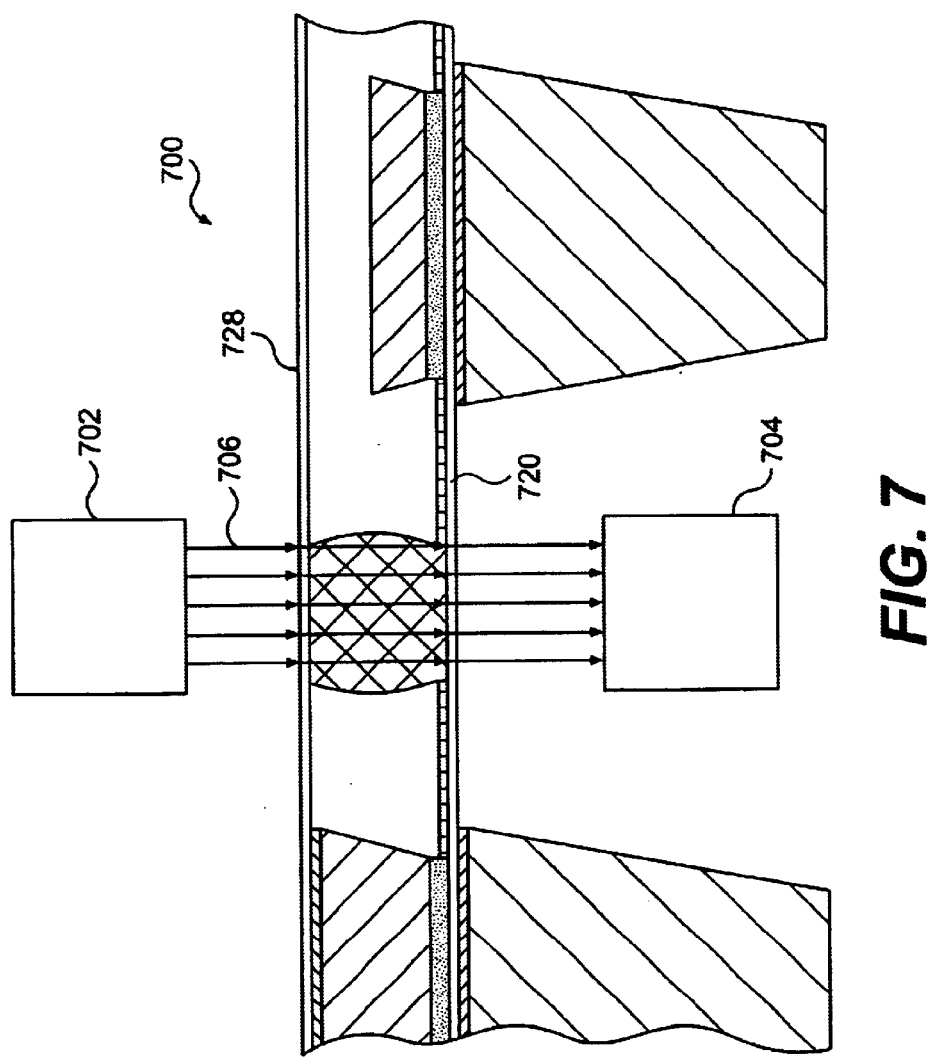
FIG. 7 is a schematic diagram illustrating the detection of crystals in an exemplary crystallization apparatus having two films, according to an embodiment of the present invention.

In a preferred embodiment, however, the embodiments of FIGS. 5A–5D and 6 use a sandwich drop format because it enables the detection of the presence of target compound crystals optically or with other electromagnetic radiation or x-rays, with minimal distortion. FIG. 7 illustrates an example of this detection method, with an emitter 702 (e.g., an electromagnetic radiation emitter) on one side of an apparatus 700 and a detector 704 (e.g., electromagnetic radiation detector) on the opposite side. Detection system sensitivity is optimized by flat transparent thin films 720 and 728 that hold the sample in a sandwich configuration, with the films 720 and 728 parallel and with the detection beams 706 normal to the films 720 and 728. The films are preferably transparent to the beams typically used in crystal detection systems, such as electromagnetic radiation or x-rays. The embodiments of FIGS. 5A–5D, 6, and 7 attempt to optimize the automated detection of crystals at the earliest time by enabling the assembled plates to be repeatedly scanned by a detection system without interrupting the vapor diffusion/crystal growth process.

Although embodiments of this invention illustrate apparatus having 96, 384, or 1536 test sites, it should be understood that the invention is not limited to any specific number of test sites. For example, the apparatus of the present invention can be configured with any number of test sites (e.g., 24, 48, 96, 384, 1536, 3456, etc.). Indeed, with the embodiment in which two films are used to provide the crystallization chambers, hydrophobic inks on the film can provide a large number of test sites, assuming that the corresponding small sample volumes are possible.

Unlike the crystallization devices of the prior art, the apparatus of the present invention can be used with an automatic or robotic multi-channel pipetting system that dispenses small sample volumes. The primary reason for this advantage is that, in placing samples of smaller volumes (e.g., below 1 ul), the automatic dispensing systems must physically touch off the surface onto which the sample is being dispensed (to get the sample to release from the pipette). With the prior art crystallization devices, which provide hard surfaces (e.g., polystyrene) onto which to dispense samples, this exercise cannot be accomplished easily, especially when using generic pipette tips, which can vary in length and straightness. Thus, the prior art devices can create undesirable inconsistencies in pipetting or breakdown of the automatic equipment. In contrast, with the present invention, because of the flexibility of the film, pipette tips can be pushed into the surface of the film to ensure touch off at each location. (With such operations, instead of positioning the face of the film perpendicular to the pipette tip(s), it can be desirable to angle the film, e.g., 30 degrees, to help the solution break away.) Thus, the present invention can operate with smaller volumes of protein or other precipitant, which can significantly reduce the cost of growing crystals. Moreover, the present invention is compatible with the robotic systems that dispense these small volumes.

The present invention addresses many of the needs of crystallographers, researchers, and others involved in pharmaceutical structure based drug discovery efforts. The present invention provides a fast, reliable, repeatable, and cost effective solution for screening solutions to find those that will produce crystals of a target compound. Indeed, with the present invention, a user can manually or automatically prepare thousands of experiments a day, using, for example, as little as 100 nl of protein, and can create reproducible results.

The present invention provides one or more of the following benefits:

1) Experiments can be prepared manually or with a robotic system—provides scalability;
2) Reduced drop size—saves expensive and scarce (protein) samples and produces results in hours instead of weeks and months;
3) Increased speed—96-site embodiment prepares up to 12,000 experiments per 8 hour day automated/6,000 manually, while the high density embodiments enable four and sixteen fold increases over the 96-site embodiment (with automation);
4) Near-foolproof sealing—eliminates wells lost by evaporation;
5) Smaller reaction chamber—reduces costs associated with reagents and, with high density embodiments, sample volumes are reduced ten fold or more;

6) Precision engineered and matched components—ensures proper placement of drops in wells or site locations;

7) Identification markings with pre-printed well location information—eases documentation and viewing of experimental results;

8) Innovative film usage—allows for removal of crystal samples during the experiment for closer examination and the ability to return the sample back to the original site location and reseal without disturbing adjacent sites; and 9) The 384, 1536, and 3456 high-density sandwich drop embodiments enable the use of high speed automated detection systems.

A specific application of the present invention enables a high throughput method for manually or automatically screening solutions for the crystallization of proteins to produce macro molecular crystals.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for forming crystals comprising:

depositing a screening solution into a well of a microplate;

depositing a precipitant solution onto a film; and placing the film over the well such that the precipitant solution is suspended over the screening solution.

wherein the film includes a hydrophobic mask and the precipitant solution is contained within the hydrophobic mask.

2. The method of claim 1, wherein the film is sealed to the well.

3. The method of claim 2, wherein the film is sealed to the well with a sealant between the film and the well.

4. The method of claim 1, wherein placing the film includes inverting the film.

5. A method for forming crystals comprising:

depositing a screening solution onto a first film;

depositing a precipitant solution onto the first film proximate to the screening solution;

sealing the screening solution and the precipitant solution within a site between the first film and a second film; and providing, within the site, an air gap between the screening solution and the precipitant solution.

6. The method of claim 5, further comprising determining whether crystals are present.

7. The method of claim 6, wherein determining whether crystals are present comprises using an automated detection system.

8. The method of claim 7, wherein the automated detection system uses one of electromagnetic radiation and as a means of detection.

9. The method of claim 5, wherein sealing the screening solution and the precipitant solution comprises:

supporting the second film with a lattice structure having a first through-hole, a second through-hole, and a passageway connecting the first through-hole and the second through-hole;

disposing the screening solution within the first through-hole;

disposing the precipitant solution within the second through-hole; and sealing the first film and the second film to opposite sides of the lattice structure.

10. The method of claim 5, further comprising containing the screening solution and the precipitant solution within a hydrophobic mask on the first film.

11. The method of claim 5, wherein sealing the screening solution and the precipitant solution comprises placing the second film over the first film with a support structure separating the first film from the second film.

12. The method of claim 5, wherein sealing the screening solution and the precipitant solution comprises inverting the first film and placing the first film over the second film.

13. The method of claim 12, further comprising containing the screening solution and the precipitant solution within a hydrophobic mask on the first film.

14. The method of claim 13, wherein the hydrophobic mask holds the screening solution and the precipitant solution at locations on the first film aligned with through-holes of a support structure that supports the second film.

15. A method for identifying solutions that enable crystal growth of a compound comprising:

depositing a plurality of screening solutions into wells of a microplate;

depositing a plurality of precipitant samples onto a film at positions corresponding to the wells of the microplate, wherein each precipitant sample comprises a mixture of a solution of the compound and the screening solution in the corresponding well; and placing the film over the microplate such that the precipitant samples are suspended over their corresponding wells.

16. The method of claim 15, further comprising observing at least a portion of the plurality of precipitant samples through the film to determine if crystal growth has occurred.

17. A method for identifying solutions that enable crystal growth of a compound comprising:

depositing a plurality of screening solutions onto a first film at discrete sites;

depositing a plurality of precipitant samples onto the first film, wherein each individual precipitant sample of the plurality of precipitant samples is adjacent to a corresponding screening solution at its discrete site, and wherein each individual precipitant sample comprises a mixture of a solution of the compound and the corresponding screening solution;

placing a second film over the first film such that the plurality of precipitant solutions and the plurality of screening solutions contact the second film;

sealing each individual precipitant sample and its corresponding screening solution within its discrete site; and providing, at each discrete site, an air passage between the individual precipitant sample and its corresponding screening solution.

18. The method of claim 17, further comprising scanning the discrete sites to identify sites with crystals.

19. The method of claim 18, wherein the discrete sites are scanned with one of electromagnetic radiation and x-rays.

20. A method for identifying solutions that enable crystal growth of a compound comprising:

providing a first film with a plurality of discrete sites, wherein each discrete site contains two or more subsites;

depositing a plurality of screening solutions onto the first film at one or more subsites of each discrete site;

depositing a plurality of precipitant solutions onto the first film at one or more subsites of each discrete site, such that the one or more subsites of each discrete site contain at least one precipitant sample and at least one screening sample, wherein the at least one precipitant sample comprises a mixture of the solution of the compound and the at least one screening sample;

placing a second film over the first film such that the plurality of precipitant solutions and the plurality of screening solutions contact the second film;

at each discrete site, sealing the at least one precipitant sample and the at least one screening sample within its discrete site; and providing an air passage between the subsites of each discrete site.

21. The method of claim 20, further comprising scanning the plurality of discrete sites to identify sites with crystals.

22. The method of claim 21, wherein the plurality of discrete sites is scanned with one of electromagnetic radiation and x-rays.

* * * * *

UNITED STATES PATENT AND TRADEMARK OFFICE
CERTIFICATE OF CORRECTION

PATENT NO. : 6,767,401 B2
APPLICATION NO. : 10/345217
DATED : July 27, 2004
INVENTOR(S) : Richard H. Goodwin, Jr.

It is certified that error appears in the above-identified patent and that said Letters Patent is hereby corrected as shown below:

At claim 8, column 12, line 9, insert -- x-rays -- after the "and"

Signed and Sealed this

Twenty-ninth Day of July, 2008

JON W. DUDAS
*Director of the United States Patent and Trademark Office*